United States Patent [19]
Dandekar

[11] Patent Number: 4,777,019
[45] Date of Patent: Oct. 11, 1988

[54] BIOSENSOR

[76] Inventor: Thomas Dandekar, Rankestrasse 2, 8000 München 40, Fed. Rep. of Germany

[21] Appl. No.: 850,727

[22] Filed: Apr. 11, 1986

[30] Foreign Application Priority Data

Apr. 12, 1985 [DE] Fed. Rep. of Germany ....... 3513168

[51] Int. Cl.⁴ .......................................... G01N 27/22
[52] U.S. Cl. .................... 422/68; 324/71.5; 422/69; 422/98; 436/151; 436/806
[58] Field of Search ...... 422/69, 68, 90, 98; 436/151, 806, 94; 324/71.5

[56] References Cited

U.S. PATENT DOCUMENTS

| | | | |
|---|---|---|---|
| 4,219,335 | 8/1980 | Ebersole | 422/69 X |
| 4,236,893 | 12/1980 | Rice | 422/69 X |
| 4,238,757 | 12/1980 | Schenck | 436/151 X |
| 4,242,096 | 12/1980 | Oliveira et al. | 422/61 X |
| 4,444,892 | 4/1984 | Malmros | 436/151 X |
| 4,446,474 | 5/1984 | Mizusaki et al. | 204/1 T |
| 4,562,157 | 12/1985 | Lowe et al. | 436/806 X |
| 4,591,550 | 5/1986 | Hafeman et al. | 436/806 X |
| 4,592,894 | 6/1986 | Panitz | 422/69 |

OTHER PUBLICATIONS

Caras et al., Field Effect Transistor Sensitive to Penicillin Anal. Chem., 1980, 52, pp. 1935-1937.

Primary Examiner—Michael S. Marcus
Attorney, Agent, or Firm—Blakely, Sokoloff, Taylor & Zafman

[57] ABSTRACT

This invention introduces a new class of devices for detecting the presence of biological molecules. The construction principle of the device involves the direct introduction of small monomers of macromolecules into the surface layer of a semiconductor, for example by doping at the gate-area of a field effect transistor (or any other similar suitable electronic device, also on carbon basis). There are a few biological monomers which pair specifically enough for a selective measurement, such as nucleotides (or portions thereof, e.g. adenine, thymine, guanine, cytosine and uracil). This invention leads to substantial improvement of biosensors, as there should be: Better signal to noise ratio, and options for: reading of nucleotide sequences, better process control, and new synthesis possibilities (e.g. modified Merrifield Synthesis). The invention also offers the potential to construct cybernetic systems and true biochips.

4 Claims, 1 Drawing Sheet

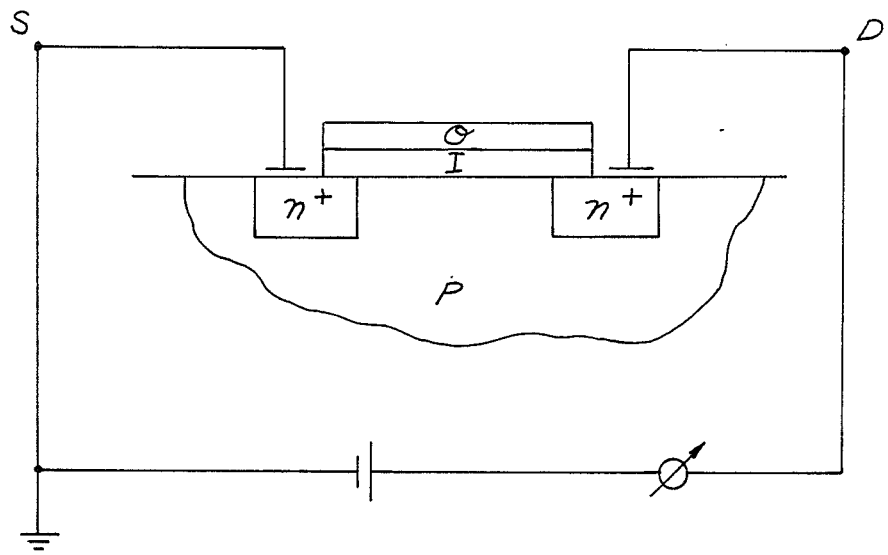
*Fig. 1*
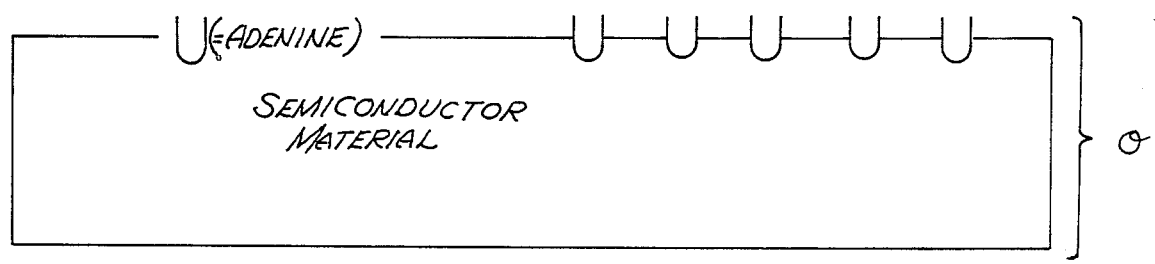
*Fig. 2*
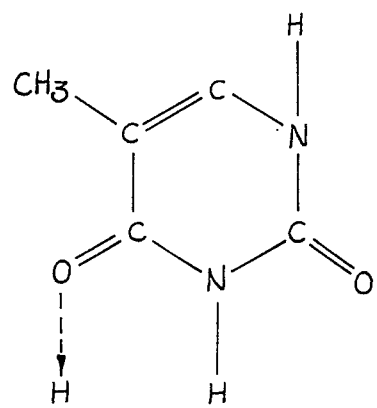
*Fig. 3*
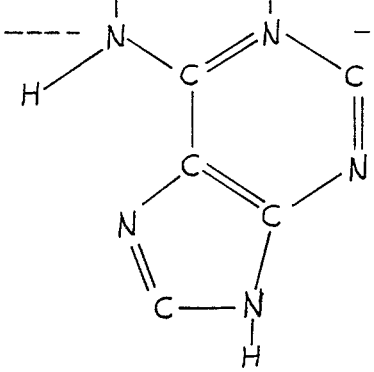
THYMINE
ADENINE

BIOSENSOR

BACKGROUND OF INVENTION

1. Field of the Invention

The invention concerns biosensors, i.e. sensing devices, in which biological molecules (e.g. enzymes) measure other substances which change the electrical properties of an electronic part (e.g. a semiconductor in a field effect transistor).

2. Relevant Technology and Literature

The concept of the biosensor has been known for a long time. A first application was the Malathion-(nerve-gas) sensor (Guilbaut, 1961). Immobilized cholinesterase was placed between two platinum-grids. The hydrolysis of the constantly added substrate (acetylcholin) is reduced in the presence of nerve-gas and thus an electronic signal created. Relevant literature includes: Sensors with the combination microbe-transistor (e.g. Karube Isao, Suzuki Shinchi "Biosensor for Fermentation and environmental control", Biotech 83, U.K. 83, pp. 625–632); Enzym-piezo-electrical crystal sensor (e.g. Cooper, Jeffrey B. et al., "Piezoelectric Sorption Anesthetic Sensor" in: IEEE Transactions on biomedical Engineering, USA 1981, Vol. BME-28 No. 6, pp. 459–466); Ionselective field effect transistor (e.g. Mc-Kinley, B.A. et al., "in vivo continuous monitoring of K+ in animals using ISFET probes", Med. Instruments (Baltimore), 14 (2) 1980)); Caras, S. and Janata Jiri, "field effect transistor sensitive to penicillin", Analytial Chem. USA 1980, 52, pp. 1935–1937; Schenk, John F. "FET for detection of biological reactions", U.S. Pat. No. 4,238,757; The combination of antibody and FET is also important J. Giaever, U.S. Pat. No. 3,853,469; Cox, U.S. Pat. No. 3,831,432; Umezawa Yoshi, Liposome immunoelectrode (Antibody signal enhanced via a complement-marker species), Proc. of the Int. Meeting on Chem. Sensors, Fukuoka, Japan, Sept. 19-22 1983); This collection is not complete, for further information consider e.g. Clermann, Robert J., "State of the art survey: Biochips" Technology 82 W00034; The MITRE Corp., USA 1982; and New Biosensor Devices, Biotech 83, U.K. 1983.

The signal from a biosensor should be as strong and as specific as possible. This led, after the first beginnings noted above, to the usage of macromolecules, e.g. enzymes or antibodies, and even bacteria, to get an electronic signal out of a biochemical (e.g. a sugar concentration) signal. These macromolecules have a high specific recognizing capability (antibody recognizes with high specificity its antigenic determinant). In practical applications, ions and foreign proteins interfere with the recognition of substances by these macromolecules. The great dimensions and complex structure of the macromolecules offer plenty opportunity for such an interference.

Besides this the dimension of the molecules used makes a direct implantation of the organic layer into the electronic layer impossible. An interfacing layer is used to get a connection between biological and electronic layer. The required wider separation between biological layer and electronic layer enhances the susceptibility to substantially interfering noise and increases the danger of losing the macromolecules not tightly enough bound at the organic layer (which is a limitation of the usage and life time under practical conditions).

A biosensor tries to convert a biological chemical signal (especially concentrations of biochemical substances) into an electronic signal (thus measuring it). To achieve this most efficiently a low signal to noise ratio is critical. This is an important practical problem for such devices. Further important practical problems are a long life and use-time and simple and low cost production of such biosensors. The invention shall help to ease these problems.

SUMMARY OF THE INVENTION

This invention tries to solve the above mentioned problems by fixing the biological part of the biosensor as close as possible to the electronic part. The problem is solved according to the invention by directly introducing the biological part into the electronic semiconductor layer, e.g. by doping of the upper layers of the semiconductor, especially the surface itself. This is only possible if very small molecules are used. These molecules have normally only unsatisfactory sensor properties, i.e., they have no specific binding properties. The most important exclusion of this fault are nucleotides, purines or pyrimidines, which have comparatively high pairing specificity with small dimensions (evolutionary selection forced the development of such molecules). The technically simplest solution is the combination of a field effect transistor with adenine (or any nucleotide). The pairing of adenine with thymine creates a quite different electrostatic field in contrast to free adenine or unspecifically excited adenine. Thus an adenine doped field effect transistor (doping in the gate area of field effect transistor) is able to measure the concentration of thymine in the solution (different field around the gate modulates, via the gate, the source-drain current through the FET). It is not necessary to use the usual techniques for doping (see e.g. Dziewior, J. Transport and Rekombinationsprozesse in hochdotiertem Silizium, Dissertation 1980, Stuttgart), if there are other ways of introducing the nucleotide, or portion thereof, for example adenine, in the upper layers of a semiconductor without impairment of the pairing properties of adenine. The industrial production of this invention will mainly depend on finding an optimal process for the implantation of the adenine (or the nucleotide or the amino acid or the small organic monomer).

DESCRIPTION OF DRAWINGS

FIG. 1 shows a device of the invention.

FIG. 2 shows a portion of a device of the invention.

FIG. 3 shows the pairing of adenine and thymine in a device of the invention.

DETAILED DESCRIPTION OF THE INVENTION

FIG. 1 shows a simple example of the biosensor module according to the invention. That figure shows the module consisting of a field effect transistor, having an electronic part (Source has been marked by S, drain has been marked by D, the semiconductor layers are marked n (negative), p (positive), and I indicates the insulated gate layer), and a biological part (marked with an O, in the example this layer is doped with adenine). This is one example. For the production of the module according to the invention, any electronic device can be used which can transform the biochemical signal elicited by the pairing on its surface between the implanted organic molecules and a corresponding species of the solvent. In this example, the field effect transistor produces an electronic signal because the electrostatic field of adenine paired with thymine is different from adenine unpaired and the difference in electrostatic field changes the conductivity in the field effect transistor. In FIG. 1, the adenine implantation is in the layer marked O, which is separated by the thin insulated gate layer I (otherwise it is doubtful whether there will be any field built up) from the field effect transistor. The changes in the conductivity around the gate will modulate the source and drain current through the field effect transistor. In the same way, as already has been explained, any other organic molecule can be used for implantation which is small enough to be introduced into the surface layer of an electronic device and at the same time is still specific enough to interact selectively with the substrate it has to measure, in a reversible way, and creates a sufficient field effect.

FIG. 2 underlines the important difference of the invented module in contrast to a normal field effect transistor: The surface of the biological layer carries adenine molecules. In FIG. 2 the biological layer is pictured in detail (denoted by the letter O and the wide bracket). The signs "U" symbolize the adenine molecules introduced into the surface of the semiconductor (silicon nitride for best mode or silicon oxide). Each adenine has two Hydrogen bond "bridges" to pair with a suitable thymine (thymine is contained in the solvent that the biosensors shall measure in this example). For clarity the adenine molecules in the example have been drawn in ideal direction for pairing. (This is not so in reality but also not necessary; see later.)

FIG. 3 shows the measurement of thymine in a solution by an adenine doped biosensor according to the invention. The letter H denotes hydrogen, C carbon, N nitrogen, O oxygen; straight lines symbolize covalent bonds. The horizontal dashed line symbolizes the boundary of the semiconductor surface. The two dashed arrows symbolize the two hydrogen bridge bonds which are formed by the pairing of adenine and thymine during the measurement.

The adenine in the surface of the semiconductor is able to pair with the thymine using these two hydrogen bridges; the connected small conformation difference leads to an electrostatic field difference and this ultimately changes the source drain current in the field effect transistor.

In practice highest sensitivity will be achieved by making the two layers denoted by the letters I and O (FIG. 1) as small as possible. Many materials are conceivable for semiconductors; in the example silicon nitride was chosen as best mode as it is (according to present techniques) more resistant to aqueous solutions (the most practicable application of this biosensor) than silicon oxide. In practice, the adenine molecules will not be ideally oriented in the surface layer of the semiconductor. Again there can be seen the advantage of using a small molecule: the "incorrectly" oriented adenine molecules have no chance for wrong pairing, in contrast to the complex possibilities of e.g. an antibody molecule, for example. Either the two hydrogen bonds, which are the only real possible open valences, are lying in such a direction that thymine pairing is possible, or not (e.g. orientation of the open bonds against the gate), but then there is also no possible mispairing with another substance. A further design of the module according to the invention would be a covalent binding of, for example adenine, or nucleotides or purines or pyrimidines, directly to the surface of a semiconductor. Still there can be expected a high specific signal as adenine will physiologically pair only with thymine (or a purine only with pairing pyrimidine) but for a "best mode" description doping was chosen. After enough time and sufficient concentration (to a first approximation, adenine will combine with thymine proportional to thymine concentration and time) no new pairing of adenine with thymine will occur. The source and drain current will vary correspondingly and the created function of current versus time (which is typically for biosensors) shifts proportional to the concentration and makes, in this way, a measurement possible.

For the next measurement, the hydrogen bonds of adenine have to be freed again. Today, biosensors normally are submerged in a neutral buffer to achieve this (e.g. enzyme-FET biosensor). This method is ineffective. With the invention herein, various other options are possible (e.g. cybernetical system). The first idea would be to load the adenine doped layer with a sufficient high electrical charge to free the adenine molecules (i.e. the thymine molecules are no longer able to bind, because the non-covalent bond to adenine is disrupted through the great additional charge). Also this is only possible because this invention introduces biological molecules into the electronic layer itself.

It is also possible to introduce amino acids or other small molecules into the surface of the semiconductor. The signal thus derived which arises by the interactions of one amino acid fixed to the semiconductor surface with a free amino acid from the solution has not the same specificity as the pairing of nucleotides. Thus there are additional conditions necessary (e.g. certain other information on the compounds contained in the solution, tests about the specificity of the introduction of the biological part into the electronic part, use of enzymes for better signal processing). Also other small biological monomers could be conceived for a useful implantation into a semiconductor surface to derive a biosensor.

The proposed biosensor is especially useful as it makes possible an industrial production with low effort. The technique of doping is quite well established. Moreover, it is possible to minimize the dimension of a module constructed according to the invention and methods already known for VLSI could be used. The minimizing of the dimensions of the proposed biosensor will also increase the specificity of the measurement because inhomogenities of the solution are less and less disturbing for such measurements.

The specificity can be enhanced greatly by a further step. It is possible to bind Polymers to the organic monomers implanted in the surface of the semiconductor (e.g. covalent bonding). This extension is the second important step in the full application of the invention. The described biosensor can be coupled to a polymer, such as poly-Uracil-mRNA (e.g. by covalently coupling a nRNA at the surface) (for this application cloning of the wanted mRNA species is necessary to get enough quantities of this nRNA species). The total field effect of the adenine coupled to mRNA and the influence on the gate is used. Thus it is possible to specifically identify longer mRNA species or one strand of DNA sequences in accordance with the invention and measure the concentrations of these species.

For those familiar with the field the superiority of the invention is explained in more detail. Of course, there are other possibilities to identify a certain mRNA species using the complementary nucleotide sequence (e.g. Hybridization of radioactively labeled mRNA with the mRNA to measure, northern blotting and so on). In the same way, there are many other technical possibilities of biosensors conceivable to measure mRNA. A simple technique would measure a difference in the field between paired and unpaired mRNA which has been entrapped in a organic surface layer (e.g. by lectins), which is fixed to the electronic part of the biosensor (e.g. a field effect transistor) by a matching interface. All such biosensors would have to cope with the difficulties due to field disturbances and unspecific effects caused by the great distance between biological layer and electronic layer. In contrast this invention anchors biological monomers having high specificity in identifying molecules in the semiconductor surface itself and after completion of this, larger, longer sequences measuring molecules are coupled to these monomers.

The module according to the invention in this extended biosensor comprises the electronic layer and the interface, where the implanted nucleotides or purines or pyrimidines serve as a binding place for the polymers. The important advantage is the minimization of the interface to nanometer dimensions. Thus a far better signal to noise ratio can be expected and only thus is the specific measurement of a larger molecule possible. Again VLSI of such constructed chips is possible.

The invention may be used to read information from biological molecules yielding a quick transformation of biologically stored information into electronic signals, thus establishing an information processing system.

The module according to the invention may also be used for synthesis processes. This important technical application is possible using a module having directly implanted small organic monomers. For those familiar with the field, many methods for protein and nucleic acid synthesis are already known. The Merrifield synthesis techniques (Nobel prize 1984) is an example of the important progress in this field. An example of this synthesis process uses a nucleotide, which is fixed on a solid phase support in a reactive chamber. In a second step, all free nucleotide is removed from the reactive chamber and only fixed nucleotides are left. Thus the first nucleotide of a nucleotide chain to be synthesized is determined. In the next step, the second nucleotide is introduced into the reaction chamber, an intervening reaction having guaranteed a fixation of this second nucleotide only to the already fixed first nucleotide but prevents a direct reaction with the solid phase support. Afterwards remaining free second nucleotide is removed. Further nucleotides are processed in a similar fashion. This process is already industrially used. With the module according to the invention a further improvement of this process is possible: The solid phase support can be (partly) replaced by modules according to the invention. The use of the biosensor according to the invention for the modified Merrifield synthesis substitutes a small (process control) or a big portion (electronic modulation of the synthesis) of the fixed carrier carrying the growing nucleotide or peptid chain by biosensors as already described.

Several options for interaction with the synthesis process are possible. The most simple application would be the continuous process monitoring with biosensors. One of the critical questions in process quality of Merrifield synthesis is the certain removal of "free" nucleotide after each reaction step and the certain binding of the fixed nucleotide to the growing chain. Both can be checked by the biosensor, thus enhancing purity and speed of the synthesis (today, maximum length is 30–50, maximal 100 nucleotides).

It is also possible to modulate the process of nucleotide synthesis interactively by changing the electric charges on the surface of the field effect transistor. The combination of additional charges on the surface of the field effect transistor together with the specificity of the semiconductor layer doped with a certain nucleotide (or the growing nucleotide chain) makes a coupling and uncoupling of specifically recognized (through pairing) nucleotide sequences possible. Thus by a full technical application of these two functions, (i.e. the monitoring of the removal of free nucleotide and the coupling and uncoupling of nucleotide to the growing sequence of nucleotides), it is possible to electronically regulate the nucleotide synthesis process. (For those familiar with the field it is obvious that such a perfection of the module according to the inventions needs a sophisticated semiconductor architecture, as there are additional channels necessary in the gate area which carry a strong modulating current to achieve the uncoupling and perhaps coupling of additional nucleotides to the nucleotide or purine or pyrimidine doped module (or with a certain nucleotide sequence extended module).

The measurement and control of protein synthesis is possible using the invention. An example of this application uses a module which is exended by a certain mRNA species; the field effect change during protein synthesis on this mRNA is monitored. At first, measuring of the field effect difference between ribosome loading and unloading on the mRNA is possible (process control), but the signals derived will yield additionally more specific information on the process by adequate investigation. (Those familiar with the field know that the measured field effect will be mainly a result from the dipole effects arising from the induction and dipoles of the various amino acid residues of the growing chain thus creating a complex, non linear signal). Again, it is useful to have only one mRNA species in the reaction chamber to have a definite signal, most elegantly achieved by in vitro translation systems. A further development would be the cybernetical loop of an adjustment or changing of the biosensor by the proteins leads to a further electronic signal by producing charged ions or the modification of the biosensor surface by enzymatic processes, and so on).

The proposed biosensor is a practical device for a biological memory. Also see: F. L. Carter, "Further considerations on molecular electronic devices", NRL Progr. on electroactive polymers; Scnd. ann. Rep., USA 1980; F. L. Carter, "Conformational switching at the molecular level", Proc. of the workshop on "molecular" electronic devices USA 1981; A. Aviram, Molecular Components for electronic device function: An overview, Biotech 83, Northwood, UK 83; A. Aviram, et al., Organic Memories, U.S. Pat. No. 3,833,894. The invention has the advantage in contrast to the ideas cited in these references to show a practicable way for the construction of such a device as the parts for the invention are already well known (field effect transistor, doping). It is also important that this inventin in contrast to the ideal mentioned above uses not newly designed organic molecules but uses the already biologically optimized nucleotides for building a memory device. (It is no accident that the above ideas are synthetic molecules which are close to nucleotide structure).

EXAMPLES OF BIOSENSORS

1. A Biosensor consisting of a semiconductor of silicon (electronic part) and nucleotides or purines or pyrimidines (or amino acids or small organic molecules which are monomers for biological macromolecules), characterized by the following: The connection between the electronic part and biological part is established through direct implantation (especially doping, but as well through covalent coupling directly in or at the semiconductor surface) of the nucleotides or purines or pyrimidines (or amino acids or small organic molecules which are monomers of macromolecules) in the electronic layer (surface and surface parts, especially above/in the gate area of a field effect transistor or a similar suitable electronic device). In addition, this device is characterized by the option to bind bigger organic molecules, especially the macromolecules physiologically derived from the monomers, e.g. covalent, at the above mentioned biological monomers which form the biological part of the biosensor.) In addition, this device is characterized as a biosensor which is able measure nucleotides and (see following) nucleotide sequences.

2. Another device of the invention is a biosensor, as described in "1" above, which is used as a device to read information from biological molecules (e.g. nucleic acids or proteins). This is an example of an information processing device using the principle of a biosensor.

3. Another device of the invention is a biosensor, as described in "1" above, which is used to construct a device for the synthesis of nucleic acids (or amino acid sequences or sequences of small organic monomers for a large biological macromolecule). This is an example of a synthesizing device using the principle of a biosensor.

4. Another device of the invention is a biosensor, as described in "1" above which is used to construct a device able to read and to store information from and to biological molecules, especially nucleic acids. This is an example of a cybernetic device using a biosensor according to the invention.

5. Another device of the invention is a biosensor, as described in "1" above, which is constructed using as electronic part from a semiconductive carbon compound (e.g. a protein produced by genetic engineering). Such a "biochip" uses small organic molecules especially nucleotides or purines or pyrimidines, which are the basis for bigger macromolecules, for the transformation of the biochemical signal (e.g. concentration of a nucleotide) into an electronic signal in the semiconductor carbon compound. (This enables the construction of a true biochip according to the definition in the proceedings of the Workshop on "molecular" electronic devices, USA, 1981).

I claim:

1. A field effect device for sensing biological monomers which pair with high specificity with complementary biological monomers comprising:
   a semiconductor body having a first doping polarity;
   a source region and a drain region each having a second doping polarity and being disposed in said semiconductor body, and said source and said drain regions defining an area in said semiconductor body between said source region and said drain region;
   an insulated semiconductor gate overlying at least a portion of said area between said source and drain regions, said insulated semiconductor gate being doped with complementary biological monomers wherein the conductivity of said field effect device is modulated by the presence of biological monomers when said biological monomers are exposed to said insulated semiconductor gate.

2. A device according to claim 1 wherein said complementary biological monomer is selected from the group consisting of a purine, pyrimidine and nucleotide.

3. A device according to claim 1 wherein some of the complementary biological monomers are disposed on the surface of said insulated semiconductor gate to facilitate pairing with said biological monomers.

4. A device as in claim 1 wherein said insulated semiconductor gate includes an organic semiconductor which is doped with said complementary biological monomer.

* * * * *